United States Patent [19]
Green et al.

[11] Patent Number: 6,060,452
[45] Date of Patent: May 9, 2000

[54] ANALOGS OF L-GLU-L-TRP HAVING PHARMACOLOGICAL ACTIVITY

[75] Inventors: Lawrence R. Green, Tacoma, Wash.; Nickolay V. Sinackevich, St. Petersburg, Russian Federation

[73] Assignee: Cytran, Inc., Kirkland, Wash.

[21] Appl. No.: 09/055,051

[22] Filed: Apr. 3, 1998

Related U.S. Application Data

[63] Continuation-in-part of application No. 08/614,764, Mar. 13, 1996, abandoned.

[51] Int. Cl.[7] .............................. A61K 38/00; C07K 4/00
[52] U.S. Cl. ................................ 514/19; 514/2; 514/300; 530/300; 530/868; 424/184.1; 424/185.1; 260/998.2
[58] Field of Search ...................... 260/998.2; 424/184.1, 424/185.1; 514/2, 19; 530/300, 868

[56] References Cited

U.S. PATENT DOCUMENTS

| | | | |
|---|---|---|---|
| 5,070,076 | 12/1991 | Morozov et al. | 514/21 |
| 5,143,903 | 9/1992 | Polita et al. | 514/18 |
| 5,538,951 | 7/1996 | Morozov et al. | 514/19 |
| 5,728,680 | 3/1998 | Morozov et al. | 514/19 |

FOREIGN PATENT DOCUMENTS

| | | |
|---|---|---|
| WO 92/17191 | 10/1992 | WIPO . |
| WO 93/08815 | 5/1993 | WIPO . |
| WO 94/20063 | 9/1994 | WIPO . |
| WO 95/03067 | 2/1995 | WIPO . |
| WO 97/12625 | 4/1997 | WIPO . |

*Primary Examiner*—Bennett Celsa
*Attorney, Agent, or Firm*—Townsend and Townsend and Crew

[57] ABSTRACT

This invention provides analogs of L-Glu-L-Trp and methods of using them for immunomodulation and treatment of pathological neovascular conditions. The analogs include the substitution of a carbon atom for a nitrogen atom in the indole ring of tryptophan.

38 Claims, No Drawings

ANALOGS OF L-GLU-L-TRP HAVING PHARMACOLOGICAL ACTIVITY

CROSS-REFERENCE TO RELATED APPLICATIONS

This application is a continuation-in-part of the U.S. application Ser. No. 08/614,764, filed Mar. 13, 1996, abandoned. The above-referenced patents and applications are incorporated herein by reference in their entireties for all purposes.

BACKGROUND OF THE INVENTION

This invention is directed to the field of pharmaceutical compounds and methods of use. In particular, this invention is directed to analogs of the di-peptide, L-Glu-L-Trp in which the nitrogen of the indole ring of tryptophan is substituted with a carbon. These analogs have similar immunomodulating and anti-angiogenic activity to the parent compound.

L-Glu-L-Trp, also known as thymogen, is a dipeptide known normalize immune system function. The drug was found to be the active principle in an extract of the thymus gland called thymosin. (Morozov et al., U.S. Pat. No. 5,070,076.) The dipeptide has been shown to be effective in the treatment of immunodeficient, immunodepressed or hyperactive immune states. (Khavinson et al., WO 92/17191; Khavinson et al., WO 95/03067; and Morozov et al., U.S. Pat. No. 5,538,951.) Pro-drugs of L-Glu-L-Trp, such as cyclized versions of the dipeptide or linear polymers of the dipeptide, are processed by the body into the active compound. (Khavinson et al., WO 93/08815.) Two related compounds, L-Ile-L-Trp and L-Leu-L-Trp, also have been shown to have immunomodulating properties similar to L-Glu-L-Trp. (Khavinson et al., WO 94/20063.) In addition to these properties, L-Glu-L-Trp has anti-angiogenic activity. (Green et al., WO 97/12625.)

Other related compound reported to stimulate the immune response are the tripeptide Pyr-Leu-Trp and phoshoramidon (sugar-Leu-Trp). (Polita et al., U.S. Pat. No. 5,143,903.) However, there is no report of these compounds being tested against HIV infection.

These tryptophan-containing dipeptides are believed to function, at least in part, by reversibly associating with specific cellular receptors, namely "CD2" receptors, thereby inducing conformation changes in the receptor which "trigger" intracellular mechanisms resulting in up-regulation of adenylate cyclase and an increase in AMP. They simultaneously increase the affinity of the CD2 receptor for its "target" ligand. This increase in affinity is believed to heighten the interaction between these cells and their natural ligands, thereby facilitating such interaction and encouraging cellular response to such interaction. (Khavinson et al., WO 94/20063.)

This application is related to U.S. Pat. No. 5,538,951 and to U.S. application Ser. Nos. 08/452,411, filed May 26, 1995 (issued as U.S. Pat. No. 5,728,680) and 08/415,009, filed Mar. 31, 1995 (issued as U.S. Pat. No. 5,789,384).

SUMMARY OF THE INVENTION

This invention provides analogs of L-Glu-L-Trp having several advantages over the parent compound. In these analogs, the nitrogen of the indole ring of tryptophan is replaced by a carbon. The carbon can be substituted with a variety of groups. Preferably, the carbon is saturated with hydrogen. L-Glu-L-Trp has the structure of formula 1:

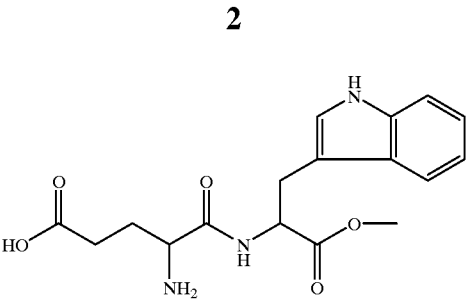

The compounds of this invention have the structure of formula 2:

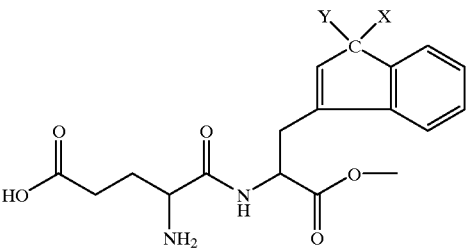

wherein X and Y are independently selected from H, lower alkyls, esters, amides, halides, carbohydrates or oligo-dideoxyribose groups, or, together can be a ketone group. The bond between X or Y and the carbon can be non-hydrolyzable. In that case, X or Y have a mass of less than about 500 D, preferably less than about 100 D. The bond between X or Y and the carbon can be hydrolyzable. In that case, any derivatization will result in an analog compound that, when exposed to water or to an enzyme that breaks a hydrolyzable bond, will convert or transform to a hydrate or ketone. Such forms are active.

These modifications to the indole ring provide several advantages. First, the analog is more resistant to oxidation, resulting in a more stable product. Second, the compound has higher lipidophilic qualities, allowing for better transport across lipid membranes, e,g., the blood brain barrier. Third, the analogs are resistant to degradation by enzymes as compared to the parent tryptophan compound, allowing for longer and higher serum levels. Fourth, the analogs have high solubility in aqueous solutions, and rapid transport across the mucous membranes, allowing for high bioavailability. Fifth, the charge and spacial distribution characteristics are similar to parent tryptophan analog, allowing for similar if not even greater biologic activity because of the greater stability in structure.

As an immunomodulator, the compounds of this invention are effective in doses of about 1 $\mu$g/kg to about 1000 $\mu$g/kg, preferably about 10 $\mu$g/kg to about 100 $\mu$g/kg. As an inhibitor of angiogenesis, the compounds of this invention are effective in doses of about 50 $\mu$g/kg to about 100 mg/kg, preferably about 100 $\mu$g/kg to about 10 mg/kg.

DETAILED DESCRIPTION OF THE INVENTION

I. Analogs of L-Glu-L-Trp

The analog compounds of this invention are selected from compounds having the following structures:
(a) a compound of formula 2;
(b) a cyclic form of the compound of formula 2;
(c) a linear or cyclic polymer of the compound of formula 2, the polymer being no more than a 10-mer;
(d) an analog of any of the foregoing wherein the Glu moiety is replaced by an Ile moiety or a Leu moiety; and (e) a derivative of any of the foregoing compounds which hydrolyses in aqueous solution into any of the foregoing compounds.

Compounds whose structure include Glu-"Trp analog" have best activity as inhibitors of angiogenesis.

Regarding cyclized forms of the compound, it is well known in the art of chemistry that peptides frequently exist in solution in equilibrium between linear and cyclized states, equilibrium favoring the linear state. Therefore, in the blood, cyclic L-Xaa-L-Trp (Xaa being selected from Glu, Leu or Ile) would tend to equilibrate into the linear form. Regarding linear or cyclic polymers of L-Xaa-L-Trp, once introduced into the body, these compounds undergo proteolytic degradation, thereby releasing the most active form of the compound, L-Xaa-L-Trp.

Derivatives of L-Glu-L-Trp also are useful in the treatments of this invention. In one embodiment, a derivative is a pharmaceutically acceptable salt of the above compounds. A "pharmaceutically acceptable salt" is a salt that can be formulated into a compound for pharmaceutical use including, e.g., metal salts (sodium, potassium, magnesium, calcium, etc.) and salts of ammonia or organic amines.

In another embodiment, a derivative is an analog in which the reactive terminal amine or carboxyl groups are derivatized with amides, imides, esters, anhydrides, ethers, methyl or ethyl-alkyl esters, alkyl, aryl or mixed alkyl/aryl moieties in which the formula weight of the entire compound is less than about 5000 Daltons or less than about 1000 Daltons. Such derivatives are expected to equilibrate into the active form by, for example, hydrolysis in the body.

II. Pharmaceutical Compositions and Modes of Delivery

The compounds of this invention preferably are delivered as pharmaceutical compositions. "Pharmaceutical composition" refers to a composition suitable for pharmaceutical use in a subject. The pharmaceutical compositions of this invention comprise a pharmacologically effective amount of a compound of the invention and a pharmaceutically acceptable carrier. "Pharmaceutically acceptable carrier" refers to any of the standard pharmaceutical carriers, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in *Remington's Pharmaceutical Sciences*, 19th Ed. (Mack Publishing Co., Easton, 1995). Preferred pharmaceutical carriers depend upon the intended mode of administration of the active agent.

The compounds of the invention can be formulated for administration in a variety of ways. Typical routes of administration include both enteral and parenteral. These include, without limitation, subcutaneous, intramuscular, intravenous, intraperitoneal, intramedullary, intrapericardiac, intrabursal, oral, sublingual, ocular, nasal, topical, transdermal, transmucosal, or anal. The mode of administration can be, e.g., via swallowing, inhalation, injection or topical application to a surface (e.g., eyes, mucus membrane, skin).

Particular formulations typically are appropriate for specific modes of administration. Various contemplated formulations include, for example, aqueous solutions, solid formulations, aerosol, gas, vapor or dry powder formulations and transdermal formulations.

A. Aqueous Solutions for Enteral, Parenteral or Transmucosal Administration

Examples of aqueous solutions include, for example, water, saline, phosphate buffered saline, Hank's solution, Ringer's solution, dextrose/saline, glucose solutions and the like. A preferred carrier for delivery of the tryptophan-containing compounds of this invention is normal (0.09%) saline solution.

The compositions can contain pharmaceutically acceptable auxiliary substances as required to approximate physiological conditions, such as buffering agents, tonicity adjusting agents, wetting agents, detergents and the like. Additives can also include additional active ingredients such as bactericidal agents, or stabilizers. For example, the solution can contain sodium acetate, sodium lactate, sodium chloride, potassium chloride, calcium chloride, sorbitan monolaurate or triethanolamine oleate. These compositions can be sterilized by conventional, well-known sterilization techniques, or can be sterile filtered. The resulting aqueous solutions can be packaged for use as is, or lyophilized, the lyophilized preparation being combined with a sterile aqueous solution prior to administration.

Aqueous solutions are appropriate for injection (e.g. intravenous injection). Aqueous solutions also are useful for enteral administration as tonics and administration to mucous or other membranes as, e.g., nose or eye drops. The composition can contain the compound in an amount of about 1 $\mu$g/ml to about 10 mg/ml, more preferably about 10 $\mu$g/ml to about 1 mg/ml, e.g., about 100 $\mu$g/ml.

B. Solid and Other Non-Aqueous Compositions for Enteral or Transdermal Delivery

Solid compositions are appropriate for enteral administration. They can be formulated in the form of, e.g., pills, tablets, powders or capsules. For solid compositions, conventional solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed.

The carrier can be selected from various oils including those of petroleum, animal, vegetable or synthetic origin, for example, peanut oil, soybean oil, mineral oil, sesame oil, and the like. Suitable pharmaceutical excipients include starch, cellulose, talc, glucose, lactose, sucrose, gelatin, maltose, rice, flour, chalk, silica gel, magnesium stearate, sodium stearate, glycerol monostearate, sodium chloride, dried skim milk, glycerol, propylene glycol, water, ethanol, and the like.

A unit dosage form, such as a tablet, can have about 1 $\mu$g to about 100 mg of the compound.

C. Topical Administration for Transdermal or Transmucosal Delivery

Systemic administration can also be by transmucosal or transdermal means. Transmucosal delivery is particularly attractive for treatment of HIV infection because it can be self-delivered easily.

For transmucosal or transdermal administration, penetrants appropriate to the barrier to be permeated can be used in the formulation. Such penetrations are generally known in the art, and include, for example, for transmucosal administration, bile salts and fusidic acid derivatives. In addition, detergents can be used to facilitate permeation. Transmucosal administration can be through nasal sprays, for example, or using suppositories. Transdermal delivery systems can include, e.g., patches.

For topical administration, the agents are formulated into ointments, creams, salves, powders and gels. In one embodiment, the transdermal delivery agent can be DMSO. The compound can be administered in a toothpaste.

D. Delivery by Inhalation

For inhalation, the compound is preferably administered in the form of an aerosol or mist. For aerosol administration, the compound preferably is supplied in finely divided form along with a surfactant and propellant.

The surfactant preferably is soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol, and the polyoxyethylene and polyoxypropylene derivatives of these esters. Mixed esters, such as mixed or natural glycerides, can be employed. The surfactant can constitute 0.1%–20% by weight of the composition, preferably 0.25%–5%.

The balance of the composition is ordinarily propellant. Liquefied propellants are typically gases at ambient conditions, and are condensed under pressure. Among suitable liquefied propellants are the lower alkanes containing up to 5 carbons, such as butane and propane; and preferably fluorinated or fluorochlorinated alkanes. Mixtures of the above can also be employed. In producing the aerosol, a container equipped with a suitable valve is filled with the appropriate propellant, containing the finely divided compounds and surfactant. The ingredients are thus maintained at an elevated pressure until released by action of the valve.

A nebulizer or aerosolizer device for administering compounds of this invention typically delivers a dose of about concentration of between about 1 $\mu g/m^3$ and about 10 $mg/m^3$.

E. Other Formulations

In preparing pharmaceutical compositions of the present invention, it can be desirable to modify the complexes of the present invention to alter their pharmacokinetics and biodistribution. For a general discussion of pharmacokinetics, See, *Remington's Pharmaceutical Sciences*, supra, Chapters 37–39. A number of methods for altering pharmacokinetics and biodistribution are known to one of ordinary skill in the art. Examples of such methods include protection of the complexes in vesicles composed of substances such as proteins, lipids (for example, liposomes), carbohydrates, or synthetic polymers.

The tryptophan-containing compounds of this invention also can be incorporated into foodstuffs. This includes solid foods, such as cereals or chewing gums, as well as liquid foodstuffs, such as mixing the compound with hot water as a tea, or incorporating it in any other beverage. The compound may be incorporated in a soap for transdermal delivery during washing.

III. Prophylactic or Therapeutic Treatments

This invention provides methods for the prophylactic or therapeutic treatment of a number of conditions, including immune system disorders, infections, tissue damage, toxemia or anemia during pregnancy and enhancement of vaccination.

"Infection" refers to the multiplication of a parasitic organism, e.g., a virus, in a cell or in the body. A subject is "infected" with an organism if the subject has detectable amount of the organism or antibodies that specifically bind to the organism in their body. A "subject" of treatment is a mammal, including a human. Non-human animals subject to diagnosis or treatment include, for example, domesticated animals such as cats. "Treatment" refers to prophylactic treatment or therapeutic treatment. A "prophylactic" treatment is a treatment administered to a subject who does not exhibit signs of a disease or exhibits only early signs for the purpose of decreasing the risk of developing pathology. A "therapeutic" treatment is a treatment administered to a subject who exhibits signs of pathology for the purpose of diminishing or eliminating those signs.

IV. Treatments of Immunodeficient, Immunodepressed or Hyperactive Immune States This invention provides methods for treating an immune system disorder, e.g., an immunodeficient, immunodepressed or hyperactive immune state, in subject, e.g., human. The method comprises administering to the subject a pharmacologically effective amount of a compound of this invention. In one embodiment, the hyperactive immune state is an autoimmune disease. In one embodiment, the subject suffers from eczema, psoriasis, allergy or bronchial asthma. In another embodiment, the subject has been subject to thymectomy. In another embodiment, the subject has an immunodepressed state resulting from exposure to radiation, e.g. in the treatment of cancer.

V. Treatments of Infectious Diseases

This invention provides methods for the treatment of an infectious disease in an animal subject. The method comprises administering to the subject a pharmacologically effective amount of a compound of this invention. The establishment of infection frequently involves a deficiency in the immune system. Therefore, normalizing immune system function has the effect of decreasing the likelihood of developing infection or, once established, inhibiting infection. Also, the compounds of this invention are useful in inhibiting viral replication, in particular, retroviral replication, in the body. The infection can be a viral infection, bacterial infection or parasitic infection.

In one embodiment, the disease results from infralymphatic infection, a gynecological infection or a skin infection. In another embodiment, the disease is lymphangitis, an acute respiratory disease, sinusitis or parsinusitus, Otitis media, conjunctivitis, uveitis, keratitis, dental caries, gingival disease, is periapical granuloma. In another embodiment, the infection is a viral disease selected from herpes infection, herpes Type I or Type II infection, Herpes Zoster infection, influenza virus infection Type A or Type B, Hepatitis A or Hepatitis B infection or hemorrhagic dengue fever. In another embodiment the disease is Hansen's disease, typhus of the para A or B category, tuberculosis of the lung, yersenia, pseudo-tuberculosis or Shigella dysentery. In another embodiment, the disease is malaria.

VI. Treatment of Tissue Damage

This invention provides a method for the therapeutic treatment of tissue damage in an animal subject. The method comprises administering to the subject a pharmacologically effective amount of a compound of the invention.

In one embodiment, the tissue damage results from a burn or frost bite. In another embodiment, the tissue is corneal tissue.

VII. Treatment of Toxemia or Anemia During Pregnancy

This invention provides a method for treating toxemia or anemia in an animal subject during pregnancy. The method comprises administering to the subject a pharmacologically effective amount of a compound of this invention.

VIII. Treatment for Enhancing the Effect of Vaccination

This invention provides a method for enhancing the effect of a vaccination to a disease in an animal subject. The method comprising the step of administering to the subject a pharmacologically effective amount of a compound of this invention.

IX. Treatment of Pathological Conditions Involving Pathologic Neovascularization This invention provides a method of treating a subject having a pathologic condition involving neovascularization. The method involves administering a pharmacologically effective amount of a compound of this invention.

In one embodiment, the condition is hemangioma. In another embodiment the condition is vascularized malignant tumor or vascularized benign tumor. In another embodiment, the condition is neovascularization in post-recovery cerebrovascular accident; neovascularization due to head trauma; restenosis following angioplasty; or neovascularization due to heat or cold trauma. In another embodiment, condition is neovascularization associated with substance-induced neovascularization of the liver, angiogenic dysfunction related to an excess of hormone; neovascular sequelae of diabetes; neovascular sequelae to hypertension; or chronic liver infection. In another embodiment the subject suffers from AIDS and Kaposi's sarcoma.

The present invention provides novel analogs of L-Glu-L-Trp and methods for their use. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. By their citation of various references in this document Applicants do not admit that any particular reference is "prior art" to their invention.

What is claimed is:

1. A compound with the structure:

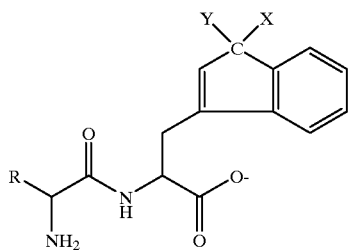

wherein X and Y are independently selected from the group consisting of:
   hydrogen, lower alkyls, esters, amides, halides, carbohydrates and oligodideoxyriboses, or wherein X and Y combine to form a keto group;
wherein the molecular weight of X or Y is less than about 500 Daltons;
wherein R is independently selected from the group consisting of:
   the side chains of Glu, Leu, and Ile; and
wherein said compound is a free acid or a pharmaceutically acceptable salt.

2. The compound of claim 1 wherein the molecular weight of X or Y is less than about 100 Daltons.

3. The compound of claim 1 wherein X and Y are both hydrogen.

4. The compound of claim 1 wherein R is the side chain of Glu.

5. The compound of claim 1 wherein X and Y are both hydrogen, and wherein R is the side chain of Glu.

6. The compound of claim 1 wherein X and Y are both hydrogen, wherein R is the side chain of Glu, and which compound is a sodium salt.

7. The compound of claim 1 wherein X and Y are both hydrogen, wherein R is the side chain of Glu, and which compound is a pharmaceutically acceptable salt selected from the group consisting of: metal salts, salts of ammonia, and organic amines.

8. The compound of claim 7, wherein the metal salts are selected from the group consisting of: potassium, sodium, magnesium and calcium.

9. A compound with the structure of:

wherein X and Y are independently selected from the group consisting of:
   hydrogen, lower alkyls, esters, amides, halides, carbohydrates and oligodideoxyriboses, or wherein X and Y combine to form a keto group;
wherein the molecular weight of X or Y is less than about 500 Daltons;
wherein R is independently selected from the group consisting of:
   the side chains of Glu, Leu, and Ile; and
wherein said compound is a free acid or a pharmaceutically acceptable salt.

10. The compound of claim 9 wherein the molecular weight of X or Y is less than about 100 Daltons.

11. The compound of claim 9 wherein X and Y are both hydrogen.

12. The compound of claim 9 wherein R is the side chain of Glu.

13. The compound of claim 9 wherein X and Y are both hydrogen, and wherein R is the side chain of Glu.

14. The compound of claim 9 wherein X and Y are both hydrogen, wherein R is the side chain of Glu, and which compound is a sodium salt.

15. The compound of claim 9 wherein X and Y are both hydrogen, wherein R is the side chain of Glu, and which compound is a pharmaceutically acceptable salt selected from the group consisting of: metal salts, salts of ammonia, and organic amines.

16. The compound of claim 15, wherein the metal salts are selected from the group consisting of: potassium, sodium, magnesium and calcium.

17. A polypeptide which is a linear or cyclic polymer of a dipeptide wherein the dipeptide has the structure of:

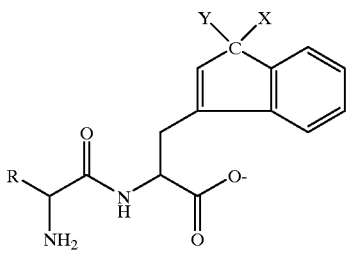

wherein X and Y are independently selected from the group consisting of:
hydrogen, lower alkyls, esters, amides, halides, carbohydrates and oligodideoxyriboses, or wherein X and Y combine to form a keto group;
wherein the molecular weight of X or Y is less than about 500 Daltons;
wherein R is independently selected from the group consisting of:
the side chains of Glu, Leu, and Ile; and
wherein said compound is a free acid or a pharmaceutically acceptable salt; and
wherein the polymer is no more than a 20-mer.

18. The compound of claim 17 wherein the molecular weight of X or Y is less than about 100 Daltons.

19. The compound of claim 17 wherein X and Y are both hydrogen.

20. The compound of claim 17 wherein R is the side chain of Glu.

21. The compound of claim 17 wherein X and Y are both hydrogen, and wherein R is the side chain of Glu.

22. The compound of claim 17 wherein X and Y are both hydrogen, wherein R is the side chain of Glu, and which compound is a sodium salt.

23. The compound of claim 17 wherein X and Y are both hydrogen, wherein R is the side chain of Glu, and which compound is a pharmaceutically acceptable salt selected from the group consisting of: metal salts, salts of ammonia, and organic amines.

24. The compound of claim 23, wherein the metal salts are selected from the group consisting of: potassium, sodium, magnesium and calcium.

25. A compound with the structure:

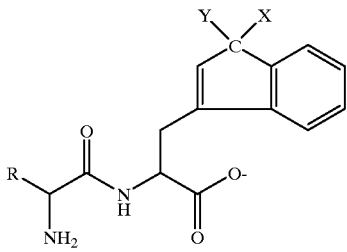

said structure having an amino terminus or carboxy terminus where said amino terminus or carboxy terminus has been derivatized with a moiety independently selected from the group consisting of: anhydrides, ethers, methyl-alkyl esters, ethyl-alkyl esters, alkyl groups, aryl groups, and mixed alkyl/aryl groups;
wherein X and Y are independently selected from the group consisting of:
hydrogen, lower alkyls, esters, amides, halides, carbohydrates and oligodideoxyriboses, or wherein X and Y combine to form a keto group;
wherein the molecular weight of X or Y is less than about 500 Daltons;
wherein R is independently selected from the group consisting of:
the side chains of Glu, Leu, and Ile;
wherein said compound is a free acid or a pharmaceutically acceptable salt; and
wherein the entire formula weight of the said compound is less than about 5000 Daltons.

26. The compound of claim 25 wherein the molecular weight of X or Y is less than about 100 Daltons.

27. The compound of claim 25 wherein X and Y are both hydrogen.

28. The compound of claim 25 wherein R is the side chain of Glu.

29. The compound of claim 25 wherein X and Y are both hydrogen, and wherein R is the side chain of Glu.

30. The compound of claim 25 wherein X and Y are both hydrogen, wherein R is the side chain of Glu, and which compound is a sodium salt.

31. The compound of claim 25 wherein X and Y are both hydrogen, wherein R is the side chain of Glu, and which compound is a pharmaceutically acceptable salt selected from the group consisting of: metal salts, salts of ammonia, and organic amines.

32. The compound of claim 31, wherein the metal salts are selected from the group consisting of: potassium, sodium, magnesium and calcium.

33. A pharmaceutical composition comprising an amount of a compound of any of the claims 1, 3, 4, 5, 6, 7, 17, or 25 effective for immunomodulation or inhibiting angiogenesis and a pharmaceutically acceptable carrier.

34. The pharmaceutical composition of claim 33 comprising 0.001% to 0.01% by weight of the compound.

35. The pharmaceutical composition of claim 33 in the form of an aqueous solution or an injectable solution.

36. The pharmaceutical composition of claim 33 in the form of an eye film, an inhalant, a mucosal spray, a toothpaste, an ointment, a tablet, a suppository, a capsule or a water soluble based cream.

37. The pharmaceutical composition of claim 33 in unit dosage form comprising about 1 µg to about 100 mg of the compound.

38. The pharmaceutical composition of claim 33 in unit dosage form comprising about 10 µg to about 100 µg of the compound.

* * * * *